US006627663B2

(12) United States Patent
Easterling

(10) Patent No.: US 6,627,663 B2
(45) Date of Patent: Sep. 30, 2003

(54) NONINVASIVE METHOD FOR TREATING HEMANGIOMAS THROUGH TRANSDERMAL DELIVERY OF CALCIUM CHANNEL BLOCKER AGENTS AND MEDICAMENT FOR USE IN SUCH METHOD

(75) Inventor: W. Jerry Easterling, 8400 Blanco Rd., Ste. 204, San Antonio, TX (US) 78216

(73) Assignee: W. Jerry Easterling, San Antonio, TX (US)

( * ) Notice: Subject to any disclaimer, the term of this patent is extended or adjusted under 35 U.S.C. 154(b) by 0 days.

(21) Appl. No.: 09/839,570

(22) Filed: Apr. 20, 2001

(65) Prior Publication Data

US 2002/0028234 A1 Mar. 7, 2002

Related U.S. Application Data

(63) Continuation-in-part of application No. 09/514,796, filed on Feb. 28, 2000, now abandoned, which is a continuation-in-part of application No. 09/128,103, filed on Aug. 3, 1998, now Pat. No. 6,031,005.

(51) Int. Cl.[7] .................. A61K 31/137
(52) U.S. Cl. .................. 514/654
(58) Field of Search .................. 514/520, 211, 514/654

(56) References Cited

U.S. PATENT DOCUMENTS

| | | | | |
|---|---|---|---|---|
| 4,338,300 A | | 7/1982 | Gelbard | 424/94.67 |
| 5,139,944 A | | 8/1992 | Sawyer | 435/226 |
| 5,242,391 A | | 9/1993 | Place | 604/60 |
| 5,474,535 A | | 12/1995 | Place | 604/60 |
| 5,569,678 A | | 10/1996 | Lee | 514/171 |
| 5,719,167 A | * | 2/1998 | Doshi et al. | 514/337 |
| 5,731,339 A | | 3/1998 | Lowrey | 514/400 |
| 5,773,020 A | | 6/1998 | Place | 424/426 |
| 5,750,141 A | | 10/1998 | Roberts | 424/449 |
| 5,902,609 A | | 5/1999 | Lee | 424/646 |
| 6,031,005 A | * | 2/2000 | Easterling | 514/654 |
| 6,113,939 A | | 10/2000 | Place | 424/430 |

FOREIGN PATENT DOCUMENTS

| | | |
|---|---|---|
| WO | WO 91/01624 | 2/1991 |
| WO | WO 91/05497 | 5/1991 |
| WO | WO 94/02130 | 2/1994 |
| WO | WO 94/17839 | 8/1994 |
| WO | WO 96/29987 | 10/1996 |

OTHER PUBLICATIONS

De Vries et al., Inflammation, 19(2), 261–75 (Apr., 1995) (abstract).*

Jain et al., International Journal of Pharmaceutics, 130(2), 169–177 (1996) (abstract).*

Diez et al., J. Pharm. Sci., 80(10), 931–934 (1991) (abstract).*

Slovis et al., European Respiratory Journal, 12(1), 240–4 (Jul., 1998) (abstract).*

Paranjothy et al., Indian Journal of Pharmaceutical Sciences, 59(2), 49–54 (1997) (abstract).*

Steinmetz et al., Cancer Causes and Control, 2(6), 427–42 (Nov., 1991) (abstract).*

Levine, et al.; "Intralesional Verapamil Injection for the Treatment of Peyronies Disease"; Journal of Urology; vol. 151, 1522–1524; 1994.

Levine; "Treatment of Peyronie's Disease with Intralesional Verapamil Injection"; Journal of Urology; vol. 158, 1395–1399; 1997.

Rehman, et al.; "Use of Intralesional Verapamil to Dissolve Peyronie's Disease Plaque: A Long–Term Single–Blind Study"; Urology, vol. 51, 620–626; 1998.

Willmann et al.; "Lecithin Organogel as Matrix For Transdermal Transport of Drugs"; Journal of Pharmaceutical Science; vol. 81, No. 9; 1992.

Riedl et al.; "Iontophoresis for the Treatment of Peyronie's Disease"; Journal of Endourology, vol. Suppl1; 1997.

Sekine et al.; "Gelointment of Verapamil for Percutaneous Absorption"; Drug Design and Delivery 1 (3): 245–52; 1987.

Jain et al.; "In Vitro Percutaneous Absorption of Verapamil"; Indian Journal of Experimental Biology 34 (5); 475–7; 1996.

Verapamil. The Merck Index (12th Edition); Entry No. 10083; 1996.

* cited by examiner

*Primary Examiner*—Phyllis G. Spivack
(74) *Attorney, Agent, or Firm*—David G. Henry

(57) ABSTRACT

The invention is of a noninvasive method for treating hemangiomas involving the topical application of verapamil suspended in a carrier through which penetration of verapamil is enhanced.

5 Claims, No Drawings

NONINVASIVE METHOD FOR TREATING HEMANGIOMAS THROUGH TRANSDERMAL DELIVERY OF CALCIUM CHANNEL BLOCKER AGENTS AND MEDICAMENT FOR USE IN SUCH METHOD

CITATION TO PRIOR APPLICATION

This is a continuation-in-part with respect to U.S. application Ser. No. 09/514,796 filed Feb. 28, 2000, abandoned, which was a continuation-in-part of U.S. application Ser. No. 09/128,103, filed Aug. 3, 1998, now U.S. Pat. No. 6,031,005, from which application and its parent application priority is here claimed under 35 U.S.C. §120.

BACKGROUND OF THE INVENTION

1. Field of The Invention

The present invention relates to the treatment of hemangiomas.

2. Background Information

Hemangioma is the most common benign tumor of infants. They are usually apparent at birth but become evident within the first two weeks. Hemangiomas occur in 5–10% of all children and three times more often in females then males.

Approximately thirty percent of all hemangiomas are visible at birth. The remaining seventy percent become visible within one to four weeks after birth. Hemangiomas occur 5 times more often in females than in males and occur predominantly in Caucasians. Low birthweight infants (less than 2.2 pounds) have a twenty six percent chance of developing a hemangioma.

Approximately eighty three percent occur on the head and neck area. The remaining seventeen percent appear throughout the the rest of the body (both externally and internally). In the early stages some appear either as bluish or reddish spots or flat patches. Rarely is a hemangioma fully grown at birth.

Hemangiomas that are flat and appear reddish in color are called "superficial" and those that are deep beneath the skin and appear bluish in color are called "deep" hemangiomas. When a hemangioma is both deep and superficial it is called a "compound" hemangioma Hemangioma will grow for the first 8–12 months of life. Growth can be prolific and may appear to change daily. Hemangiomas will begin to regress or involute around 12 months of age. This process may take up to 10–12 years leaving residual scarring.

While all hemangiomas eventually involute the result is not always cosmetically acceptable. Early intervention has been shown to reduce the need for corrective surgery after "involution" has occurred; or to, at least, minimize extensive corrective surgeries in the future. Psycho-social scarring an which occurs when a child has been forced to live with a facial deformity until "involution" has been completed can be avoided by early, aggressive intervention, according to presently known treatment options.

Conventional treatment options for hemangiomas range from surgical excision (followed, in cases of facial or neck hemangiomas, with cosmetic surgery) to systemic corticosteroid treatments, laser, and use of alpha-interferon, Recently, cryosurgery and sclerotherapy, have been proposed additions to the available treatment regimens for hemangiomas.

Each conventional treatment option carries potential side effects. Clearly, surgery always presents risks, whether for infection, unexpected patient reaction to anesthesia, and/or unexcpected aesthetic results.

While systemic corticosteroid treatment is suspected of certain side effects (or, at least, its safety has never been fully substantiated, according to some authorities), regardless of age, steroid treatment carries decided risks if carried on beyond a child's first birthday. Furthermore, hemangiomas do not warrant nor benefit from steroids beyond the first birthday, in part, because proliferation of hemangiomas tends to end by that point anyway. In any event, if steroids are lowered too quickly or given intermittently, "rebound growth" is possible, if not likely. Some investigators have reported other side effects from steroid treatments. In one investigation, children (29 percent) became more irritable, depressed and/or napped less during treatment, although this resolved as treatment was tapered and discontinued. Other short-term side effects included gastric irritation, oral or perineal yeast infection, recurrent otitis media, hypertension, and myopathy.

The disadvantages of sclerotheraphy include the pain of injection, swelling, and psychological strain associated therewith, as well as the danger of necrosis if the sclerosis technique is flawed.

While certain treatments for hemangiomas are considered typically effective, the psychological effects of hemangiomas alone warrant the relentless pursuit of more effective treatment regimens for hemangiomas, whether for use alone, or in concert with existing treatment options. Also, because most patients receiving treatments are infants or small children, patient tolerance for the treatment options becomes of more paramount importance.

In view of the above, a substantial contribution to humanity would come in the form of any new and improved treatment options directed to hemangiomas. Such a new and improved treatment option for hemangiomas would ideally embody characteristics which are beneficial, at least when compared to existing treatment options, with respect to efficacy, long-term side effects, patient discomfort during treatment, and residual aesthetic or cosmetic consequences,

SUMMARY OF THE INVENTION

It is an object of the present invention to provide an improved treatment regimen for hemangiomas.

It is another object of the present invention to provide an improved treatment regimen for hemangiomas, which treatment regimen obviates the need for surgery, steroid treatment, or other treatment modalities with known potential side effects and/or treatment risks or discomfort.

It is another object of the present invention to provide an improved treatment regimen for hemangiomas, which treatment regimen is based on the use of a pharmacological agent known to have minimal potential side effects.

It is another object of the present invention to provide an improved treatment regimen for hemangiomas, which treatment regimen obviates, at least in part, the need for all but a mere topical application of a therapeutic medicament.

In satisfaction fees and related objects, the present invention provides for the treatment of hemangiomas through the periodic topical application of a calcium channel blocker agent which is combined with an agent for facilitating transdermal penetration thereof.

DETAILED DESCRIPTION OF THE PREFERRED EMBODIMENT

In the preferred embodiment of the present medicament, and in the medicament upon which the associated method are based, the primary active ingredient is Verapamil Hydrochloride, USP (a diphenylalkylamine). However, it should be understood that other calcium channel blocker agents (topically applied in a similar composition to that taught herein) provide similar, if not indistinguishable results when treating a variety of amber and fibrotic tissue manifestations. Therefore, it is contemplated that the transdermal administration through topical application of calcium channel blocker agents suspended in a penetration enhancing agent will, regardless of the species of the calcium channel blocker agent(s), exhibit efficacy in treating hemangiomas. Today, patient trials have been conducted through the use of the herein described verapamil-based topical gels, with very favorable and prompt results (visible changes observed within a matter of weeks). Other calcium channel blocker agents which could supplement or substitute for verapamil include benzothiazepines (Diltiazem, for example), dihydropyridines (Amlodipine, Felodipine, Isradipine, Nicardipine, Nifedipine, Nimodipine, or Nisoldipine), and the fast sodium inward channel inhibitor—Bepridil.

I. Preparation.

The preferred Verapamil-based gels of the present invention (in exemplary 10% and 15% percent strengths) may be prepared according to the following disclosure and protocol, with variations appropriate to a desired scale of production as will be apparent to persons skilled in the production of pharmaceutical preparations:

A. Constituents of Preferred Embodiment of Topical Verapamil Gel 10% and 15%

| Ingredients | 10% (% W/W) | 15% (% W/W) |
|---|---|---|
| Verapamil | 10.0 | 15.0 |
| Ethoxydiglycol | 14.0 | 19.5 |
| Propylene Glycol | 0.5 | 0.5 |
| Butylated Hydroxy Toluene (BHT) | 0.1 | 0.1 |
| Lecithin Soya Granular | 13.1 | 13.1 |
| Isopropyl Myristate | 13.1 | 13.1 |
| Sorbic Acid | 0.09 | 0.09 |
| Pluronic F127 | 9.8 | 11.6 |
| Potassium Sorbate | 0.15 | 0.12 |
| Disodium Edetate | 0.01 | 0.01 |
| Purified Water | 39.15 | 26.88 |

B. Topical Verapamil 15% (To Make 3000 Gm).

| Ingredients | Quantity |
|---|---|
| Verapamil HCI USP | 450.00 Gm |
| Ethoxydiglycol Reagent | 585.0 Gm |
| Lecithin/Isopropyl Myristate Solution | 790.0 Gm |
| Butylated Hydroxytolune NF (BHT) | 3.0 Gm |
| Edetate Disodium USP | 0.30 Gm |
| Propylene Glycol USP | 15.0 Gm |
| Pluronic Gel 30% | 1,156.7 Gm |

Instructions: Dissolve verapamil in ethoxydiglycol and propylene glycol with the aid of heat (90–100 degrees C.). Stir during this dissolving step. When the solution is clear, weigh to ascertain the amount of evaporation. Add the amount lost to evaporation back as ethoxydiglycol. Immediately add the lecithin/isopropyl myristate and BHT and stir well. Weigh the PLO 30% into a plastic container, add edetate disodium and stir gently to dissolve edetate disodium. Avoid foaming with stirring. Gently add the verapamil phase to the PLO phase, avoiding the incorporation of air. Stir for 10 minutes using a 3 inch mixing blade at 3100 rpm. Dispense in 30 Gm glaminate ointment tubes.

C. Topical Verapamil 10% (To Make 3000 Gm).

| Ingredients | Quantity |
|---|---|
| Verapamil HCI USP | 300.00 Gm |
| Ethoxydiglycol Reagent | 420.0 Gm |
| Lecithin/Isopropyl Myristate Solution | 790.0 Gm |
| Butylated Hydroxytolune NF (BHT) | 3.0 Gm |
| Edetate Disodium USP | 0.30 Gm |
| Propylene Glycol USP | 15.0 Gm |
| Pluronic Gel 30% | 1,471.7 Gm |

Instructions: Dissolve verapamil in ethoxydiglycol and propylene glycol with the aid of heat (90–100 degrees C.). Stir during this dissolving step. When the solution is clear, weigh to ascertain the amount of evaporation. Add the amount lost to evaporation back as ethoxydiglycol. Immediately add the lecithin/isopropyl myristate and BHT and stir well. Weigh the PLO 30% into a plastic container, add edetate disodium and stir gently to dissolve edetate disodium. Avoid foaming with stirring. Gently add the verapamil phase to the PLO phase, avoiding the incorporation of air. Stir for 5 minutes using a 3 inch mixing blade at 3100 rpm. Dispense in 30 Gm glaminate ointment tubes.

D. Pluronic Gel 20% (To Make 3000 Gm)

| Ingredients | Quantity |
|---|---|
| Pluronic F127 NF (Poloxamer 407) | 600.00 Gm |
| Potassium Sorbate NF | 9.00 Gm |
| Water (Sterile for Irrigation) qs to | 3,000.00 Gm |

Directions: Prepare a pluronic gel by combining the potassium sorbate and pluronic F 127 and bringing to a total weight of 3,000 Gm. with cold (refrigerated) sterile water. Make sure that all the granules are wet, and place in a refrigerator. Mixture will form a clear solution over 24–48 hours.

Alternate Procedure: The above mixture can be uniformly mixed with a mixing blade. It will take on the appearance of beaten egg whites. When placed in the refrigerator it will form a clear solution much faster, usually overnight.

The above solution will solidify into a clear gel at room temperature.

E. Pluronic Gel 30% (To Make 2000 Gm).

| Ingredients | Quantity |
|---|---|
| Pluronic F 127 NF (Poloxamer 407) | 600.00 Gm |
| Potassium Sorbate NF | 6.00 Gm |
| Water (Sterile for Irrigation) qs to | 2,000.00 Gm |

Instructions: Prepare a pluronic gel by combining the potassium sorbate and pluronic F 1 27 and bringing to a total weight of 2,000 Gm. with cold (refrigerated) sterile water. Make sure that all the granules are wet, and place in a refrigerator. Mixture will form a clear solution over 24–48 hours.

Alternate Procedure: The above mixture can be uniformly mixed with a mixing blade. It will take on the appearance of beaten egg whites. When placed in the refrigerator it will form a clear solution much faster, usually overnight. The above solution will solidify into a clear gel at room temperature.

F. Lecithin/Isopropyl Myristate Solution (To Make 3000 Gm).

| Ingredients | Quantity |
|---|---|
| Lecithin Soya Granular | 1,494.0 Gm |
| Isopropyl Myristate NF | 1,494.0 Gm |
| Sorbic Acid NF Powder | 9.90 Gm |

Instructions: Disperse lecithin and sorbic acid in isopropyl myristate. Allow to stand at room temperature until a liquid of syrup consistency forms. Stir well and store in a light protected container.

G. Alternative Formulations.

It is to be understood that the above formulations and preparation methodologies are merely those which are believe to be ideal based on current experience and knowledge. Hemangiomas may be successfully treated using formulations like, or substantially equivalent to those taught in the U.S. Pat. No. 6,031,005 the entirety of the disclosure of which patent is incorporated herein by reference as if set forth herein verbatim. The addition of constituents in the present medicaments over those taught in the reference to patent are included for, and relate principally to product stability, not to efficacy. Therefore, the combination of one or more calcium channel blocker agents and any penetration enhancing agent for facilitating transdermal delivery of active ingredients in the treatment of hemangiomas is within the scope of the present invention and of the appended claims.

II. Use of Preparations

The choice of strengths of the topical verpamil gels taught above will depend on the experience of the clinician, as will the duration of treatment. Ordinarily, a patent with hemangiomas will be started with the lower dosage preparation, and only if the patient fails to respond, or responds more slowing than reasonably would be expected, would the patient be changed to the higher dosage form.

In any event, use of all topical calcium channel blocker preparations of the present inventor's work involves simply applying a thin coating of the gel topically to the hemangioma, slightly overlapping onto the surrounding area, usually once daily. Clinicians will prescribe certain volumetric dosages, which dosages can be metered by any number of conventional metering means (syringes, dosimeters, blister packs, single-dose tubes, etc.)

Based on experience to date, both with hemangiomas and with other aberrant conditions with which the present medicaments have been used, it is expected that an approximate six-month treatment regimen will be required to effect a near complete involution of hemangiomas in typical patients.

Although the invention has been described with reference to specific embodiments, this description is not meant to be construed in a limited sense. Various modifications of the disclosed embodiments, as well as alternative embodiments of the inventions will become apparent to persons skilled in the art upon the reference to the description of the invention. It is, therefore, contemplated that the appended claims will cover such modifications that fall within the scope of the invention.

I claim:

1. A medicament for use in the topical, transdermal treatment of external hemangiomas comprising:

verapamil; in a carrier consisting essentially of
a lecithin/isopropyl myristate solution,
butylated hydroxy toluene,
and pluronic F127;

an antioxidant agent suspended in said carrier for preventing the oxidation of active ingredients of said medicament; and water.

2. The medicament of claim 1 further comprising:

Edetate disodium.

3. The medicament of claim 2 further comprising:

Propylene glycol.

4. The medicament of claim 1 further comprising:

Propylene glycol.

5. A method for treating an external hemangioma comprising the steps of:

selecting a medicament comprising:

verapamil; in a carrier consisting essentially of
a lecithin/isopropyl myristate solution,
butylated hydroxy toluene,
and pluronic F127;

an antioxidant agent suspended in said carrier for preventing the oxidation of active ingredients of said medicament; and water; and periodically, topically applying a therapeutic dosage of said medicament to said external hemangioma for sufficient time to effect a desired level of involution of said hemangioma.

* * * * *